(12) United States Patent
Zipplies

(10) Patent No.: US 7,600,325 B2
(45) Date of Patent: Oct. 13, 2009

(54) BONE MEASUREMENT DEVICE FOR USE DURING ORAL IMPLANT SURGERY

(76) Inventor: Robert Ernst Zipplies, Thalreit 7, Raubling (DE) 83064

( * ) Notice: Subject to any disclaimer, the term of this patent is extended or adjusted under 35 U.S.C. 154(b) by 545 days.

(21) Appl. No.: 11/643,840

(22) Filed: Dec. 22, 2006

(65) Prior Publication Data

US 2007/0209221 A1    Sep. 13, 2007

Related U.S. Application Data

(60) Provisional application No. 60/779,443, filed on Mar. 7, 2006.

(51) Int. Cl.
*A61B 5/103* (2006.01)
*A61B 5/107* (2006.01)
(52) U.S. Cl. .............. 33/514; 33/512; 600/591
(58) Field of Classification Search ........... 33/511–514, 33/836; 600/587–591, 593, 304
See application file for complete search history.

(56) References Cited

U.S. PATENT DOCUMENTS

| | | | | |
|---|---|---|---|---|
| 3,740,779 A | * | 6/1973 | Rubricuis | 33/512 |
| 4,226,025 A | * | 10/1980 | Wheeler | 33/512 |
| 4,768,953 A | * | 9/1988 | Nestor et al. | 33/514 |
| 5,070,623 A | * | 12/1991 | Barnes | 33/512 |
| 5,156,161 A | * | 10/1992 | Lollar | 33/512 |
| 5,484,447 A | * | 1/1996 | Waldock et al. | 33/511 |
| 6,213,959 B1 | * | 4/2001 | Kushida | 33/514 |
| 7,296,361 B2 | * | 11/2007 | Chi et al. | 33/512 |
| 2002/0046471 A1 | * | 4/2002 | Skidmore | 33/511 |
| 2008/0104855 A1 | * | 5/2008 | Kim et al. | 33/836 |

* cited by examiner

Primary Examiner—Yaritza Guadalupe-McCall

(57) ABSTRACT

The present invention is a tool to measure depth and width of bone cavities prior to and during oral implant placement. The tool includes a passive-depth gauge arm and an active spring caliper arm. The tool can be used to define the extraction socket for oral implant placement and allows measurement verifications after each step of the bone bed preparation prior to or during the actual implant placement in the extraction socket. There are multiple modifications of the primary design into separate embodiments to accommodate usage in different parts of the jaw and different points during the implant procedure.

20 Claims, 4 Drawing Sheets

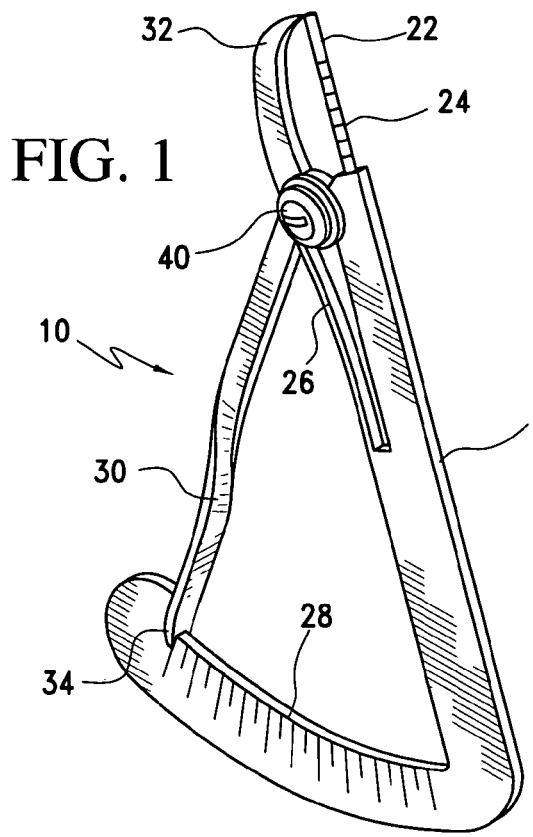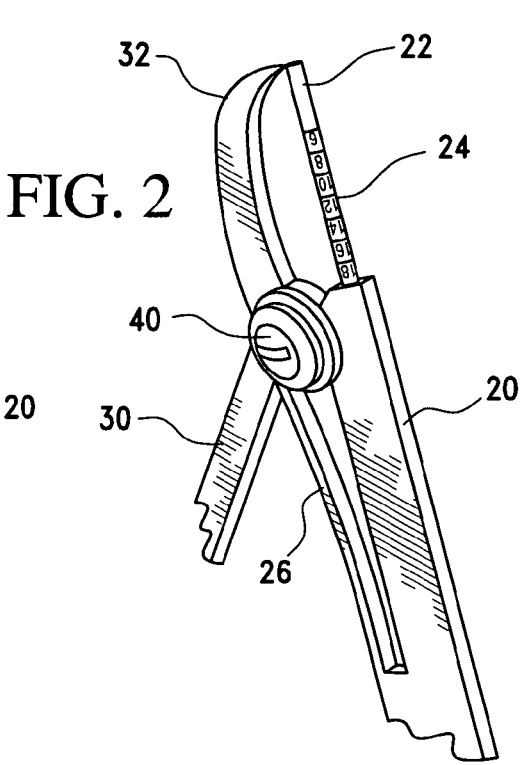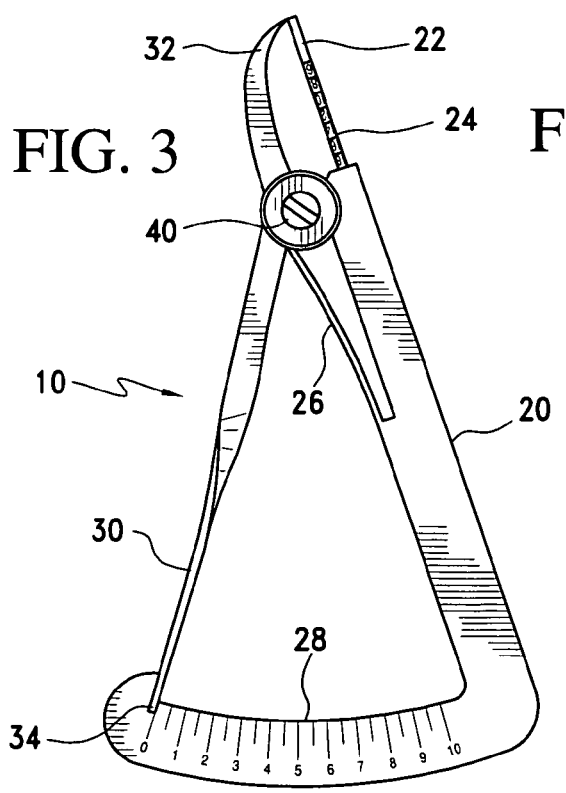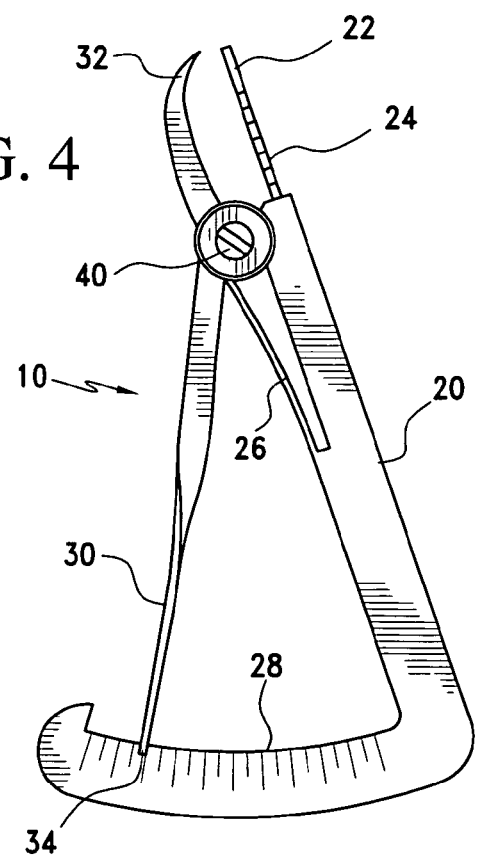

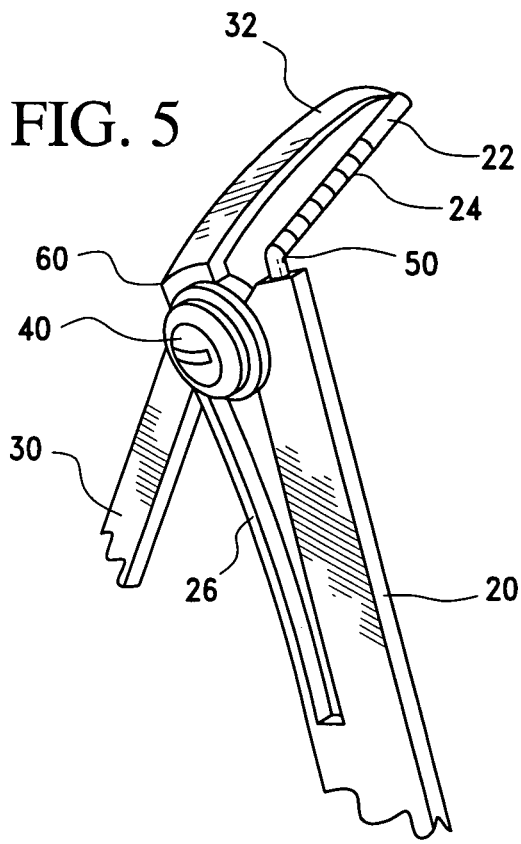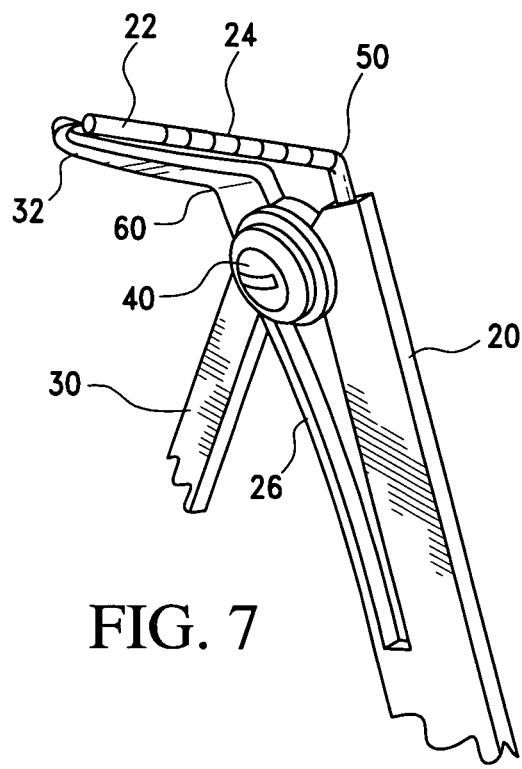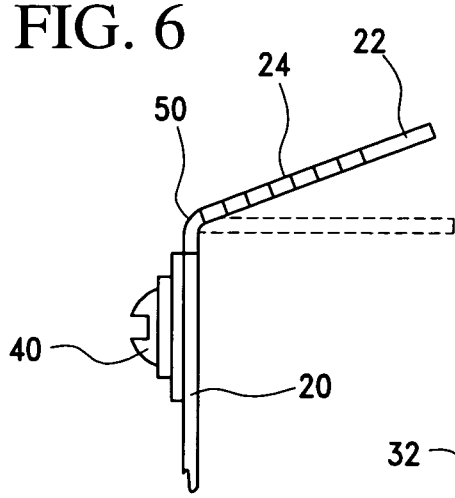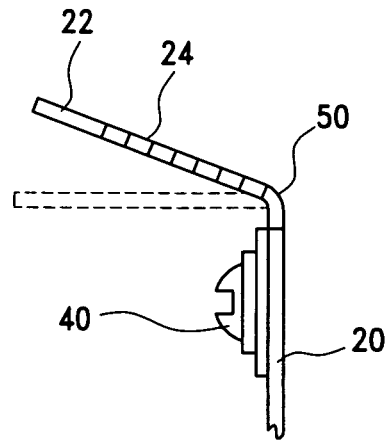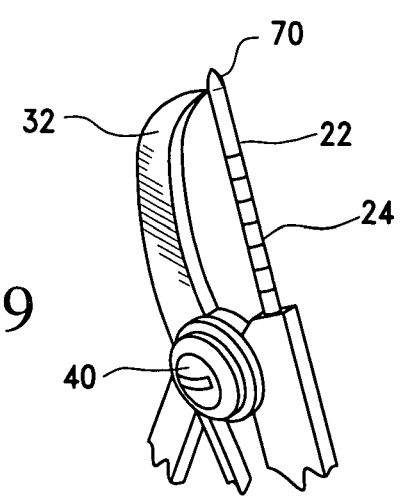

BONE MEASUREMENT DEVICE FOR USE DURING ORAL IMPLANT SURGERY

CROSS-REFERENCE TO RELATED APPLICATIONS

This application claims the benefit of U.S. Provisional Application No. 60/779,443, filed Mar. 7, 2006.

BACKGROUND OF THE INVENTION

1. Field of the Invention

The present invention combines functions for measuring depth and width in one tool for use in oral implant placement. It can be used to measure the bone cavity either immediately after the tooth extraction or at later stages directly after initial preparation of the implant cavity.

2. Description of the Related Art

The replacement of lost teeth with oral implants has proven to be the preferable treatment option for many patients. Successful oral implants help prevent healthy oral structure loss while they rehabilitate the patient both functionally and esthetically. The correct three-dimensional selection and placement of oral implants is mandatory for predictable treatment outcomes. Misplacement of an oral implant can lead to severe or even life threatening consequences (e.g., Hemorrhagic swelling of the mouth floor after accidental damage of blood vessels).

Currently, diagnostics are mostly based on panoramic X-rays and plaster jaw models. Advanced diagnostics include the bone sounding procedure, bone mapping procedure, transversal cut X-rays, and different types of CT scans. Due to distortion and magnification, conventional panoramic X-rays provide limited information. Plaster models usually do not include the basic portion of the alveolar ridge into which the oral implants are placed. Preoperative bone sounding requires an additional use of local anesthetics and does not deliver adequate results related to the preparation of the implant bed. Although CT scans deliver correct three-dimensional data of the operational site, they expose the patient to a considerable amount of radiation. Although three-dimensional planning based on CT data is highly accurate, the transfer into the operational site remains difficult and work-intensive. Furthermore, all of the diagnostics listed above provide limited guidance during the implant procedure itself.

SUMMARY OF THE INVENTION

The use of the new tool offers a series of benefits to the dentist. First, it can be used to define the potential of the extraction socket for oral implant placement, leading to increased efficiencies during surgery. Second, it allows the dentist to check the situation after each step of the bone bed preparation during or prior to the actual implant placement in the extraction socket, increasing accuracy of placement. Third, dehiscences and fenestrations of oral or vestibular bone walls can be detected and the potential need and extent for Guided Bone Regeneration (GBR) procedures can be determined early, assuring better patient outcomes. The new tool is useful in immediate implant placement procedures, early implant placement procedures or late implant placement procedures. No matter which placement protocol is applied, the new tool is always quickly available, enabling more accurate placement without either additional X-ray exposure or the time taking one requires. Multiple embodiments of the primary measurement tool all aid the accuracy and efficiency of the surgical implant procedure.

BRIEF DESCRIPTION OF THE DRAWINGS

FIG. 1 is a view of the straight embodiment shown with the tool in its closed and un-activated position.

FIG. 2 is a close-up of the closed and un-activated top of the straight embodiment.

FIG. 3 is the side view of the measurement device in its closed and un-activated position.

FIG. 4 is the side view of the straight embodiment in a partially open position.

FIG. 5 is an enlargement of the side view of the downward-angled embodiment in a closed position.

FIG. 6 is a detailed view of the joint of a downward-angled depth gauge.

FIG. 7 is an enlargement of the side view of the upward-angled embodiment in a closed position.

FIG. 8 is a detailed view of the joint of an upward-angled depth gauge.

FIG. 9 is a detailed view of a tapered gauge tip.

DETAILED DESCRIPTION OF THE INVENTION

Figure 10:
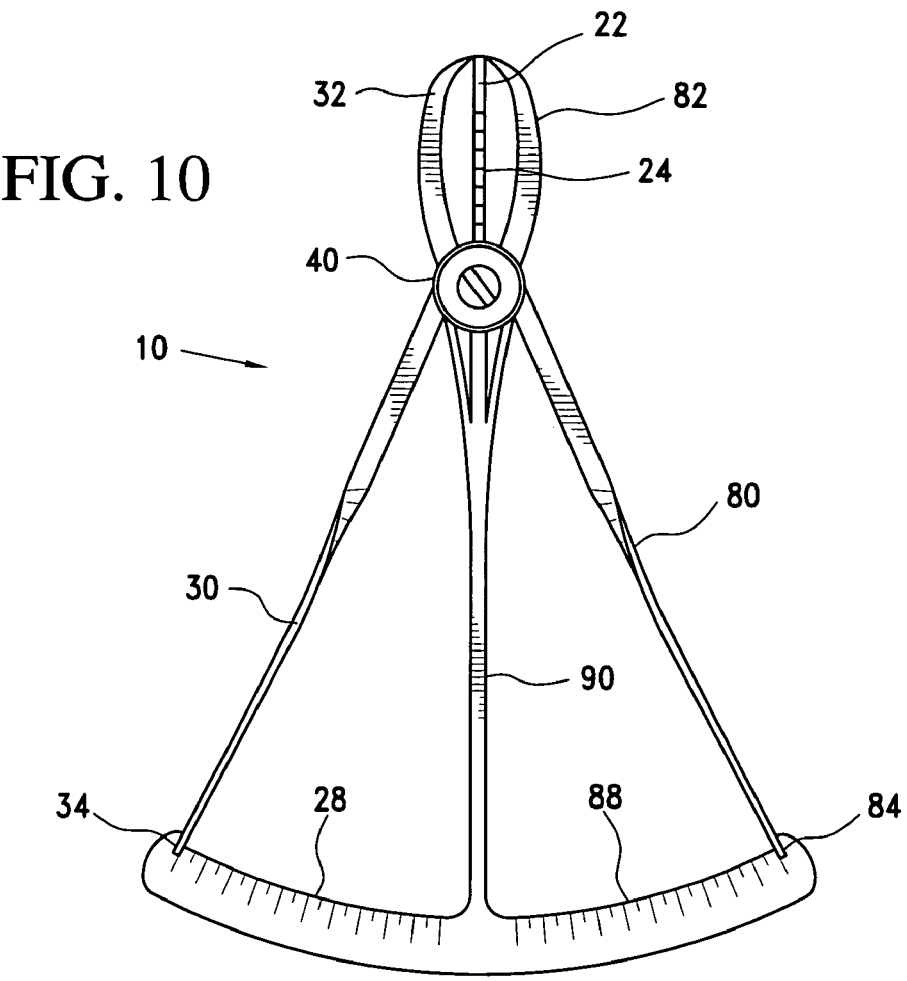
FIG. 10 is a front plan view of a double spring and single depth gauge embodiment.

FIG. 1 represents the primary embodiment of the invention. The measurement tool 10 consists of a depth gauge 22 with a passive arm 20 and a spring caliper with an active arm 30. The passive arm 20 of the depth gauge 22 has a flat or rounded top 70. The depth gauge 22 has a scale 24, preferably in millimeters, and originates at the body of the passive arm 20. The depth gauge 22 may include a removable, spring caliper tip for easy replacement of the depth gauge when the tip wears down. The body of the passive arm 20 is curved at the bottom. The scaling 28 at the bottom is for the spring caliper function. The body of the passive arm 20 gives rise to a spring 26 which applies force to the active spring caliper arm 30 under the joint 40 between the passive and active arms to keep the spring caliper closed. The top of the active spring caliper arm 32 represents the mobile part of the spring caliper function. Its continuation under the joint 40 connects it to the passive arm 20 that is under pressure from the spring 26. Toward the bottom, the active spring caliper arm 30 is twisted. At the bottom, split end 34 overlaps the width measurement scale 28 on the passive arm 20.

The new tool has a variety of uses in oral implant surgery. The first use is extraction socket measurement immediately after extraction. It works by applying finger pressure to the active arm 30, so the spring caliper function is no longer in contact with the tip of the depth gauge function. The depth gauge 22 is placed into the depth of the extraction socket until there is resistant bone at the extraction socket bottom. By releasing pressure from the active arm 30, the spring of the passive arm forces the tip 32 of the spring caliper function back into the direction of the tip of the depth gauge function. The outside of the extraction socket's bone wall resists against this force. The distance between the tip of the depth gauge function and the tip of the spring caliper function can be read from the scale 28 of the spring caliper function, representing the width of the bone wall. After measuring bone width at the bottom of the socket, force is then reapplied to the active arm 30 in order to increase the distance between the tip of the depth gauge function and the tip of the spring caliper function. The depth gauge function is repeatedly lifted upwards to the desired extent to obtain additionally required measurements. The number of measurements required depends on the thickness of the patient's bone wall. Thin walls usually require more measurements than thick walls. Lastly, the bone width at the extraction socket top is measured in the described manner. The instrument is then turned and the opposite bone wall is measured accordingly. A "0" measurement at the extraction socket top that may or may not continue further down indicates a dehiscence. Any "0" measurement at any point below measured bone indicates a fenestration.

The second use is in implant bed preparation for measuring cavity depth and bone wall width. Measurement is highly recommended to evaluate the bony surrounding of the implant bed cavity. Even using advanced protocols involving CT data-derived surgical guides, it is necessary to check the accordance of the actual drilling compared to the prior virtual planning. Any bone formation changes that occur between the time the CT is taken and when the surgery is performed, can be instantly measured and identified using this tool.

FIG. 2 is an enlarged view of the top of the device. The cut top of the depth gauge includes a depth gauge measurement scale 24, preferably in millimeters. A scale mark circles the depth gauge at intervals, such as every 2 millimeters, and may also include a measurement number for easier reading by the user of the device. The body of the depth gauge arm 20 is the origin of the spring 26 that applies force to the body of the spring caliper arm 30. The depth gauge arm 20 and the spring caliper arm 30 are connected by a joint 40. Force from the spring 26 against the spring caliper arm 30 results in the contact of the spring caliper arm tip 32 to the depth gauge arm tip 22.

FIG. 3 is a two-dimensional side view of the measurement tool described in FIG. 1, with the measurement device in its closed and un-activated position. The spring caliper function width measurement scale 28 includes markings, preferably in millimeters. When measurement tool 10 is in the closed and un-activated position, the split end 34 rests at the stop at the end of passive arm 20, giving a zero reading.

FIG. 4 shows the device 10 in a partially-open position. Any open position of the device requires force against the active spring caliper arm 30. That force has to be larger than the force of the spring 26 that originates from the body of the passive arm 20. Through this construction, the device remains closed when there is no external force applied to the device. The distance between the top of the depth gauge arm 22 and the top of the spring caliper arm 32 correlates with the position of the split end 34 of the active arm 30 on the scale 28 at the bottom of the passive arm 20.

FIG. 5 represents an enlarged view of another embodiment of the invention. In this embodiment, the top of the device is downward-angled in the range of 60 to 90 degrees to facilitate its use in rear parts of the jaws, especially the lower-right jaw buccal bone walls, lower-left jaw lingual bone walls, upper-left jaw buccal bone walls and upper-right jaw palatal bone walls. The top of the passive arm 22 is angled at point 50 along with the top of the active arm 32 at point 60. All other details remain similar to those described in FIG. 1.

FIG. 6 is an enlarged, two-dimensional side view of the top of the embodiment described in FIG. 5. The broken line indicates different degrees of angulation to include obtuse as well as acute angles.

FIG. 7 represents an enlarged view of another embodiment of the invention. In this embodiment, the top of the device is upward-angled in the range of 60 to 90 degrees to facilitate its use in rear parts of the jaws, especially the lower-right jaw lingual bone walls, lower-left jaw buccal bone walls, upper-left jaw palatal bone walls and upper-right jaw buccal bone walls. All other details remain similar to those described in FIG. 1.

FIG. 8 is an enlarged, two-dimensional side view of the top of the embodiment described in FIG. 7. The broken line indicates different degrees of angulation, to include obtuse as well as acute angles.

FIG. 9 is an enlarged view of an embodiment of the top of the depth gauge arm 22. In this embodiment, the top 70 is rounded and extends over the zero mark of the scale. The purpose of this embodiment is to be in accordance to the bone cavity that is created through the use of a drill. Most pilot drills exhibit an apical excess length, meaning that the implant bed is deeper than the depth measured at the deepest point with the full diameter. The depth gauge 22 diameters range from 0.1 to 7 millimeters.

FIG. 10 represents another embodiment of the invention. It is the combination of one depth gauge function with two spring caliper functions used to allow measurements of oral and vestibular bone walls at the same time. The body of the depth gauge arm extends at the bottom into two directions and contains two spring caliper function width measurement scales 28 and 88. The depth gauge arm 90 divides into two springs which apply force to the two active spring caliper arm bodies 30 and 80 under the joint 40. This force results in the two spring caliper function tips 32 and 82 contacting the depth gauge function tip 22. In this position, the split ends 34 and 84 of the spring caliper functions are at the zero mark of the corresponding scales 28 and 88. The spring caliper function of the first spring caliper arm 30 and function tip 32 results in measurements on scale 28 independently of the measurements on scale 88 resulting from the spring caliper function of the second spring caliper arm 80 and function tip 82.

Figure 11:
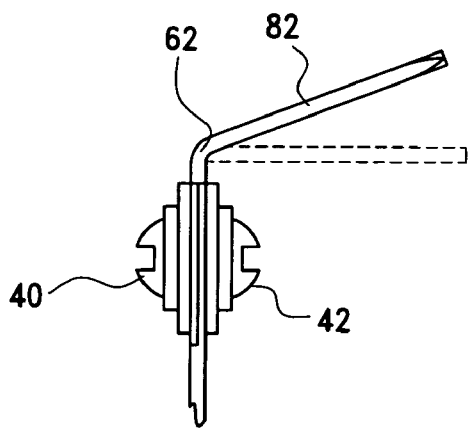
FIG. 11 is an enlarged side view of the joint between the double spring and single depth gauge of an angled top embodiment having different angulations.
Figure 12:
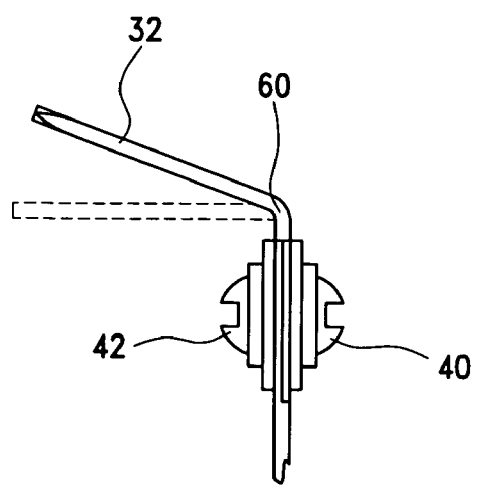
FIG. 12 is an enlarged side view of the joint between the double spring and single depth gauge of an angled top embodiment shown from the opposite side of FIG. 11.

FIGS. 11 and 12 represent the enlarged, two-dimensional views of the top of another embodiment shown from opposite sides. This embodiment differs from the embodiment described in FIG. 10 because it is angled at point 62. The broken line represents different degrees of angulation in the range of 60 to 90 degrees to include both acute and obtuse angles. The angled top facilitates using the device in rear parts of the patient's jaw. As seen by the side views, the top joint 40 controls the spring caliper function of the first spring caliper arm 30 and function tip 32 with respect to the depth gauge arm 90 having a divided spring. The bottom joint 42 controls the spring caliper function of the second spring caliper arm 80 and function tip 82 with respect to the depth gauge arm 90 having a divided spring.

The use of this tool is to measure oral bone wall width and vestibular bone wall width at the same time. It can be used in both extraction socket measurement and implant bed preparation. For certain regions of the jaw, this embodiment is a more efficient measuring tool, speeding the implant procedure. Angulations on the tool equivalent to earlier embodiments may be required to ensure efficient and accurate measurement.

Figure 13:
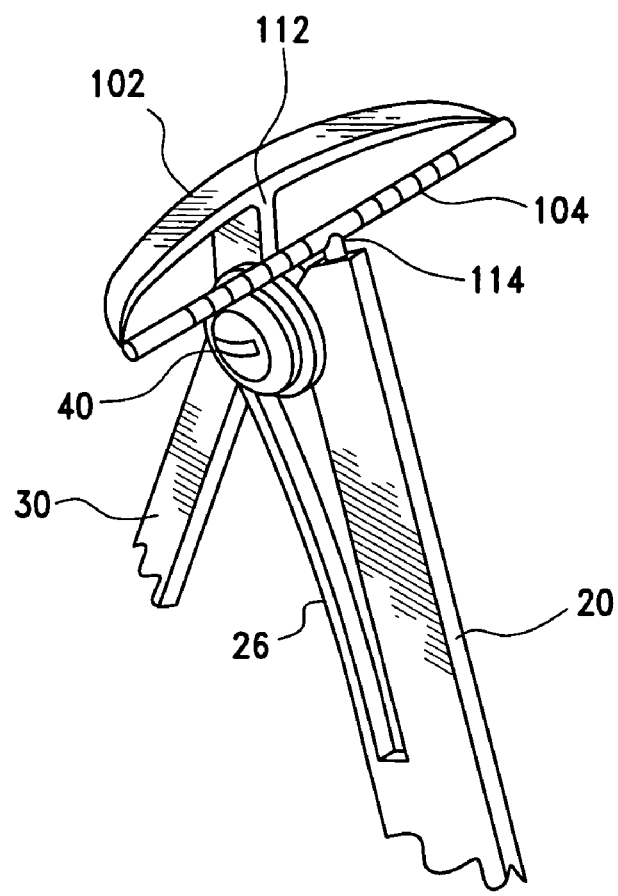
FIG. 13 is a double-ended depth gauge in combination with a double-ended spring caliper.

FIG. 13 is the enlarged view of the top of another embodiment which consists of a double-ended depth gauge 104 in combination with a double-ended spring caliper 102. The instrument is shown in a closed position where the double-ended depth gauge 104 and the double-ended spring caliper 102 are in contact. The origin 114 of the double-ended depth gauge 104 is the body of the depth gauge arm 20. The origin 112 of the double-ended spring caliper 102 is the body of the spring caliper arm 30.

Using all other embodiments, measurements are read from the scale(s) 28 (and 88). With this embodiment, bone width can be either measured by reading the scale 28 or by viewing a visual approximation demonstrated by the distance between the tip of the spring caliper function and the depth gauge outside of the bone. This embodiment is useful when the scale position that may result from jaw location is too awkward for easy viewing.

Figure 14:
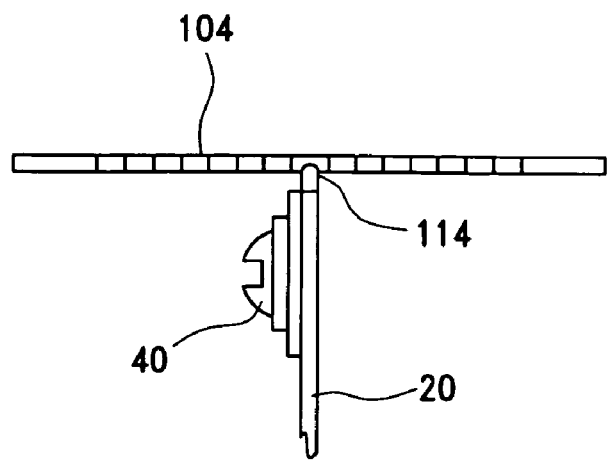
FIG. 14 is a detailed, enlarged view of the double-ended depth gauge.

FIG. 14 represents the detailed, two-dimensional side view of the embodiment described in FIG. 13. The double-ended depth gauge 104 with its origin 114 is at the top of the depth gauge arm body 20. The joint 40 connects the bodies of depth gauge arm 20 with the spring caliper arm 30.

The invention claimed is:

1. A caliper comprising:
 a passive arm including a depth gauge on a top portion of the passive arm, and a curved bottom portion, said curved bottom portion having a width measurement scale marked thereon, the width measurement scale having interval scale markings;
 a joint connector; and
 an active arm pivotally connected to the passive arm at the joint connector, having a curved portion above the joint connector and a split end at a bottom portion of the active arm, the active arm split end overlapping the passive arm width measurement scale;
 wherein the curved portion of the active arm contacts the depth gauge of the passive arm in a normally closed position, and an applied pressure to the active arm in a direction toward the passive arm causes the split end of the active arm to slide along the passive arm width measurement scale, causing the curved portion of the active arm to open a measurable width with respect to the passive arm depth gauge.

2. The caliper of claim 1, wherein the passive arm splits from a point of the arm to form a spring that applies force to the active arm under the joint connector.

3. The caliper of claim 1, wherein the depth gauge of the passive arm has scaled markings at regular intervals for measuring a distance from a tip end of the depth gauge to a scaled marking.

4. The caliper of claim 3, wherein the scaled markings of the depth gauge include numerical markings.

5. The caliper of claim 1, wherein the depth gauge is removable.

6. The caliper of claim 1, wherein the depth gauge has a rounded or flat tip end.

7. The caliper of claim 1, wherein a diameter of the depth gauge ranges from 0.1 to 7 millimeters.

8. The caliper of claim 1, wherein the depth gauge portion of the passive arm and the curved portion of the active arm are equally angled with respect to their arms.

9. The caliper of claim 8, wherein the angled portions of the depth gauge and the curved portion may be downward-angled or upward-angled with respect to their arms.

10. The caliper of claim 9, wherein the downward-angled or upward-angled angles range from 60 to 90 degrees with respect to the arms.

11. The caliper of claim 1, wherein the depth gauge is a double-ended gauge.

12. The caliper of claim 11 in combination with a double-ended spring caliper.

13. The caliper of claim 1, wherein depth and width are measured in an oral cavity.

14. A caliper comprising:
 a passive arm including a depth gauge on a top portion of the passive arm, and first and second curved bottom portions extending from a bottom portion of the passive arm in two opposing directions, the first and second curved bottom portions respectively having first and second width measurement scales marked thereon, the first and second width measurement scales having interval scale markings;
 a top joint connector;
 a bottom joint connector;
 a first active arm pivotally connected to the passive arm at the top joint connector, said first active arm having a first curved portion above the top joint connector and a first split end at a bottom portion of the first active arm, the first active arm split end overlapping the first passive arm width measurement scale; and
 a second active arm pivotally connected to the passive arm at the bottom joint connector, said second active arm having a second curved portion above the bottom joint connector and a second split end at a bottom portion of the second active arm, the second active arm split end overlapping the second passive arm width measurement scale;
 wherein the first and second curved portions of the first and second active arms contact the depth gauge of the passive arm in a normally closed position, the first and second active arms operate independently of one another, and applied pressure to the first active arm and/or the second active arm in a direction toward the passive arm causes the first split end of the first active arm and/or the second split end of the second active arm to slide along the first and second passive arm width measurement scales, respectively, causing the first and/or second curved portion of the first and/or second active arm to open a measurable width with respect to the passive arm depth gauge.

15. The caliper of claim 14, wherein the passive arm divides from a point of the arm to form first and second springs, the first spring applying force to the first active arm under the top joint connector, and the second spring applying force to the second active arm under the bottom joint connector.

16. The caliper of claim 14, wherein the depth gauge of the passive arm has scaled markings at regular intervals for measuring a distance from a tip end of the depth gauge to a scaled marking.

17. The caliper of claim 14, wherein the depth gauge ranges in diameter from 0.1 to 7 millimeters, is removable, and has a rounded or flat tip end.

18. The caliper of claim 14, wherein the depth gauge portion of the passive arm and the first and second curved portions of the first and second active arms are equally angled with respect to their arms.

19. The caliper of claim 18, wherein the angled portions of the depth gauge and the first and second curved portions may be downward-angled or upward-angled with respect to their arms.

20. The caliper of claim 19, wherein the downward-angled or upward-angled angles range from 60 to 90 degrees with respect to the arms.

* * * * *